(12) United States Patent
Kimura

(10) Patent No.: US 12,029,754 B2
(45) Date of Patent: *Jul. 9, 2024

(54) ADHESIVE SHEET FOR AFFIXATION TO BODY, HOUSED IN CONTAINER

(71) Applicant: KAO CORPORATION, Tokyo (JP)

(72) Inventor: Shohei Kimura, Sumida-ku (JP)

(73) Assignee: KAO CORPORATION, Tokyo (JP)

(*) Notice: Subject to any disclaimer, the term of this patent is extended or adjusted under 35 U.S.C. 154(b) by 667 days.

This patent is subject to a terminal disclaimer.

(21) Appl. No.: 17/282,056

(22) PCT Filed: Sep. 25, 2019

(86) PCT No.: PCT/JP2019/037449
§ 371 (c)(1),
(2) Date: Apr. 1, 2021

(87) PCT Pub. No.: WO2020/071186
PCT Pub. Date: Apr. 9, 2020

(65) Prior Publication Data
US 2021/0338712 A1    Nov. 4, 2021

(30) Foreign Application Priority Data

Oct. 5, 2018  (JP) .................. 2018-190446

(51) Int. Cl.
*A61K 33/00* (2006.01)
*A61F 13/00* (2006.01)
*A61F 13/02* (2006.01)
*A61K 9/70* (2006.01)

(52) U.S. Cl.
CPC ........ *A61K 33/00* (2013.01); *A61F 13/00063* (2013.01); *A61F 13/00076* (2013.01); *A61F 13/0276* (2013.01); *A61K 9/7046* (2013.01); *A61K 9/7053* (2013.01); *A61F 2013/00906* (2013.01); *A61F 2013/0296* (2013.01)

(58) Field of Classification Search
CPC .................................................. A61K 33/00
See application file for complete search history.

(56) References Cited

FOREIGN PATENT DOCUMENTS

| | | |
|---|---|---|
| CN | 1592627 A | 3/2005 |
| CN | 101204354 A | 6/2008 |
| CN | 101903019 A | 12/2010 |
| EP | 3 607 933 A1 | 2/2020 |
| JP | 2000-319187 A | 11/2000 |
| JP | 2005-2046 A | 1/2005 |
| JP | 2005-314298 A | 11/2005 |
| JP | 2008-50316 A | 3/2008 |
| JP | 2010-202609 A | 9/2010 |
| JP | 2012-167061 A | 9/2012 |
| JP | 2013-18719 A | 1/2013 |
| JP | 2014-62087 A | 4/2014 |
| WO | WO 2018/181930 A1 | 10/2018 |
| WO | WO 2018/186395 A1 | 10/2018 |

OTHER PUBLICATIONS

Extended European Search Report issued May 30, 2022 in European Patent Application No. 19868654.5, 11 pages.
Lichti, M., et al., "Partikelmesstechnik in der Fluidverfahrenstechnik", Chemie Ingenieur Technik, Wiley VCH.Verlag, Weinheim; DE, vol. 89, Nov. 6, 2017, pp. 1599-1610 XP71142471A (with English abstract, p. 1599).
International Search Report issued on Nov. 19, 2019 in PCT/JP2019/037449 filed on Sep. 25, 2019, 2 pages.

*Primary Examiner* — Benjamin J Packard
(74) *Attorney, Agent, or Firm* — Oblon, McClelland, Maier & Neustadt, L.L.P.

(57) ABSTRACT

Provided is an adhesive sheet for affixation to the body which is excellent in enhancement and persistence of the blood circulation promoting action, has high affixability and conformability as a sheet, and is easily and widely applicable to the body in any use situation. That is, the present invention relates to an adhesive sheet for affixation to the body housed in a container, containing the following components (A) and (B): (A) bubbles containing carbon dioxide gas in a bubble fraction of 10% or more and 40% or less, and (B) water, wherein the total area occupied by bubbles having an imaginary diameter of 5 mm or more is 10% or less, in 100% of the surface area of the adhesive sheet for affixation to the body, a content of carbon dioxide gas in the total amount of the adhesive sheet for affixation to the body is from 100 to 20,000 ppm, and the adhesive sheet for affixation to the body is sealed in a low gas-permeable container.

15 Claims, No Drawings

ADHESIVE SHEET FOR AFFIXATION TO BODY, HOUSED IN CONTAINER

FIELD OF THE INVENTION

The present invention relates to an adhesive sheet for affixation to the body housed in a container.

BACKGROUND OF THE INVENTION

Performing standing work or desk work for a long period of time may cause fatigue, lassitude, swelling, pain, and the like on each part of the body. Promotion of blood circulation by massage, stretching, bathing, and the like is widely known to be effective to eliminate these symptoms. For example, Patent Literature 1 discloses a swelling ameliorant consisting of a composition containing a carbon dioxide gas generating agent in an amount such that the carbon dioxide gas concentration in the hot water can be 60 ppm or more, and it is described that the carbon dioxide gas generating agent has a very high effect of ameliorating swelling in a short time, by acting carbon dioxide gas which enlarges capillary vessels under the conditions of high hydrostatic pressure.

It is also known that, even when no hydraulic pressure is applied on the body like bathing, the action of carbon dioxide gas on the skin promotes the blood circulation of the skin, and various carbon dioxide gases utilizing this action or cosmetics and the like into which a carbon dioxide gas generating material is blended have been investigated. For example, Patent Literature 2 discloses an effervescent skin blood circulation promoting coating agent containing hydrocarbon, carbon dioxide, and an emulsifying agent. Patent Literature 3 discloses a sheet for affixation to the body housed in a container in which a laminated sheet of a bubble gel layer or a bubble liquid layer which contains bubbles having a bubble fraction of from 5 to 50% and a resin film is sealed in a low gas-permeable container, wherein the sheet contains 30% by mass or more of gas having biological activities to the body in a space portion of the container during storage.

(Patent Literature 1) JP-A-2005-314298
(Patent Literature 2) JP-A-2005-2046
(Patent Literature 3) JP-A-2010-202609

SUMMARY OF THE INVENTION

The present invention relates to an adhesive sheet for affixation to the body housed in a container, containing the following components (A) and (B):
(A) bubbles containing carbon dioxide gas in a bubble fraction of 10% or more and 40% or less, and
(B) water,
wherein the total area occupied by bubbles having an imaginary diameter of 5 mm or more is 10% or less, in 100% of the surface area of the adhesive sheet for affixation to the body,
a content of carbon dioxide gas in the total amount of the adhesive sheet for affixation to the body is from 100 to 20,000 ppm, and
the adhesive sheet for affixation to the body is sealed in a low gas-permeable container.

The swelling ameliorant described in Patent Literature 1 described above needs to continuously maintain thermal and high hydrostatic pressure conditions for 5 minutes or more, and thus, the use situation is limited and it lacks in easiness. In addition, although the agent and the sheet described in Patent Literatures 2 and 3 utilize the blood circulation promoting effect by carbon dioxide gas, carbon dioxide gas is rapidly released to the atmosphere or metabolized in vivo after application to the body, and thus, the persistence of the increase in blood flow after application needs to be further increased, in order to ameliorate symptoms such as fatigue, lassitude, swelling, and pain of the body.

Among them, it was revealed by the present inventor that, when the sheet described in Patent Literature 3 is used for large parts in the body or parts with intense movement such as the foot, affixability and conformability to the body may be deteriorated.

That is, the present invention relates to an adhesive sheet for affixation to the body which is excellent in enhancement and persistence of the blood circulation promoting action, has high affixability and conformability as a sheet, and is easily and widely applicable to the body in any use situation.

Then, as a result of intensive studies to solve the above problems, the present inventor found that an adhesive sheet for affixation to the body which can enhance and persist the blood circulation promoting action for a long period of time while effectively increasing affixability and conformability as a sheet can be obtained by controlling the bubble fraction and the size of bubbles to a specific range while containing a specific amount of carbon dioxide gas.

By containing a specific amount of carbon dioxide gas as bubbles of specific conditions, the adhesive sheet for affixation to the body housed in a container of the present invention effectively increases affixability and conformability while retaining favorable smoothness as a sheet, and exerts excellent effects thereof in terms of fast-acting properties and persistence while effectively enhancing the blood circulation promoting effect.

DETAILED DESCRIPTION OF THE INVENTION

Hereinafter, the present invention will be described in detail.

The adhesive sheet for affixation to the body housed in a container of the present invention (hereinafter, simply referred to as "the adhesive sheet for affixation to the body") is the adhesive sheet for affixation to the body, containing the following components (A) and (B):
(A) bubbles containing carbon dioxide gas in a bubble fraction of 10% or more and 40% or less, and
(B) water,
wherein the total area occupied by bubbles having an imaginary diameter of 5 mm or more is 10% or less, in 100% of the surface area of the adhesive sheet for affixation to the body,
a content of carbon dioxide gas in the total amount of the adhesive sheet for affixation to the body is from 100 to 20,000 ppm, and
the adhesive sheet for affixation to the body is sealed in a low gas-permeable container. The adhesive sheet for affixation to the body may have the form of a sheet as described below, and when it has the form containing an aqueous gel layer and a support layer or a release layer like a gel sheet, the portion of the aqueous gel layer excluding these support layer and release layer corresponds to the adhesive sheet for affixation to the body of the present invention. The content of components other than component (A) refers to the content in the total amount of the adhesive sheet for affixation to the body excluding component (A).

The adhesive sheet for affixation to the body of the present invention contains the bubbles containing carbon dioxide gas in a bubble fraction of 10% or more and 40% or less as component (A), and the content of carbon dioxide gas in the total amount of the adhesive sheet for affixation to the body is from 100 to 20,000 ppm. The adhesive sheet for affixation to the body of the present invention is a sheet for affixing on the desired part of the body, and enhances and persists the blood circulation promoting action and alleviates fatigue, lassitude, swelling, pain in such an application part.

Note that, in the adhesive sheet for affixation to the body of the present invention, a part of carbon dioxide gas is dissolved into the sheet without forming bubbles, and other part of carbon dioxide gas is present as visible fine bubbles. Such fine bubbles present in the adhesive sheet for affixation to the body of the present invention may be controlled by the bubble fraction and the content of carbon dioxide gas in the total amount of the adhesive sheet for affixation to the body while using the total area occupied by bubbles having an imaginary diameter of 5 mm or more in 100% of the surface area of the adhesive sheet for affixation to the body as an index.

The content of carbon dioxide gas is 100 ppm or more, preferably 200 ppm or more, and more preferably 500 ppm or more in the total amount of the adhesive sheet for affixation to the body of the present invention, from the viewpoint of improving the fast-acting properties and persistence of the blood circulation promoting effect and a tingling sensation.

On the other hand, the content of carbon dioxide gas is 20,000 ppm or less in the total amount of the adhesive sheet for affixation to the body of the present invention, from the viewpoint of the balance between the blood circulation promoting effect and the pressure resistance of the low gas-permeable container, and moreover, it is preferably 10,000 ppm or less, and more preferably 3,000 ppm or less, from the viewpoint of improving the favorable solubility of carbon dioxide gas. The content of carbon dioxide gas is 20,000 ppm or less, preferably 10,000 ppm or less, more preferably 3,000 ppm or less, and still preferably 1,600 ppm or less in the total amount of the adhesive sheet for affixation to the body of the present invention, from the viewpoint of appropriately controlling the size of the bubbles containing carbon dioxide gas and effectively controlling the total area occupied by bubbles having an imaginary diameter of 5 mm or more so as not to exceed 10%, while retaining the bubble fraction within the above range.

Then, the content of carbon dioxide gas is from 100 to 20,000 ppm, preferably from 200 to 10,000 ppm, still preferably from 500 to 3,000 ppm, and still more preferably from 500 to 1,600 ppm in the total amount of the adhesive sheet for affixation to the body of the present invention.

Note that the tingling sensation refers to an irritative sensation which allows to actually feel smooth blood circulation or a warm sensation on a part of the body to which the adhesive sheet for affixation to the body of the present invention is affixed.

The content of carbon dioxide gas contained in the total amount of the adhesive sheet for affixation to the body of the present invention refers to a value obtained by placing an adhesive sheet for affixation to the body to be measured in a container with lid which contains an alkaline solution, immersing for 10 minutes, trapping as a carbonate salt in the aqueous solution, and thereafter acidifying the solution again by an acidic buffer solution, measuring the carbon dioxide gas concentration of the solution at room temperature of 25° C. by using a carbon dioxide gas electrode, and then, converting the content of carbon dioxide gas in the adhesive sheet for affixation to the body from the obtained carbon dioxide gas concentration, sheet weight, and solution volume.

The adhesive sheet for affixation to the body of the present invention contains the bubbles containing carbon dioxide gas of component (A) in a bubble fraction of 10% or more, preferably in a bubble fraction of 15% or more, more preferably in a bubble fraction of 22% or more, and still preferably in a bubble fraction of 25% or more in the adhesive sheet for affixation to the body of the present invention, from the viewpoint of improving the blood circulation promoting effect. On the other hand, the adhesive sheet for affixation to the body of the present invention contains the bubbles containing carbon dioxide gas of component (A) in a bubble fraction of 40% or less, preferably in a bubble fraction of 38% or less, more preferably in a bubble fraction of 35% or less, and still preferably in a bubble fraction of 34% or less in the adhesive sheet for affixation to the body of the present invention, from the viewpoint of adhesiveness and affixability. Then, the adhesive sheet for affixation to the body of the present invention contains the bubbles containing carbon dioxide gas of component (A) in a bubble fraction of from 10% to 40%, preferably in a bubble fraction of from 15 to 38%, more preferably in a bubble fraction of from 22 to 35%, and still preferably from 25 to 34% in the adhesive sheet for affixation to the body.

As used herein, the bubble fraction refers to the value measured and calculated by the following methods.

Since the adhesive sheet for affixation to the body of the present invention is sealed in the low gas-permeable container, the value measured within 5 minutes after opening the container and taking out the sheet from the container is used as the bubble fraction. Specifically, assuming that the specific gravity of a portion excluding bubbles is 1, the sheet taken out is cut into a rectangular shape to determine the volume (A mL) of the sheet from the length, width, and height thereof, and further, the weight (B g) is measured. Then, these are introduced into the following equation (1) to measure the bubble fraction.

$$\text{Bubble fraction (\%)} = (A-B)/A \times 100 \tag{1}$$

Note that, when the adhesive sheet for affixation to the body is further supported on the support layer or the release layer, the bubble fraction may be determined by measuring the volume and the weight without removing or peeling off these layers, and thereafter excluding the total weight of these support layer and release layer, from the viewpoint of the convenience of operation.

In the adhesive sheet for affixation to the body of the present invention, the total area occupied by bubbles having an imaginary diameter of 5 mm or more is 10% or less, in 100% of the surface area of the adhesive sheet for affixation to the body. Thus, the control of the size of the bubbles allows to efficiently supply carbon dioxide gas in the sheet to the skin and to obtain a highly persistent blood circulation promoting effect. Since the smoothness of a sheet surface can be increased by avoiding the intermixing of unnecessary coarse bubbles, the adhesiveness of the sheet can be enhanced and the affixability to the body can be effectively improved. Thus, the control of the size of the bubbles can contribute greatly to not only the enhancement of the blood circulation promoting effect and the improvement in fast-acting properties and persistence, but also an increase in affixability to the body.

Such a need to control the size of the bubbles is a new finding by the present inventor. That is, the present inventor revealed that the intermixing of various coarse bubbles in conventional carbon dioxide gas-containing sheets leads to impairments in not only the smoothness of the sheet surface but also adhesiveness and a decrease in the affixability to the body, which in turn reduces efficient supply of carbon dioxide gas in the sheet to the skin and impairs the persistence of the blood circulation promoting effect, resulting in finding of the present invention.

The bubbles present on the surface of the adhesive sheet for affixation to the body of the present invention are measured within 5 minutes after opening the low gas-permeable container described below and taking out the sheet which is the sealed content under conditions at room temperature of 25° C. and relative humidity of 50% and may be an irregular oval shape. Thus, the bubble is regarded as an imaginary circle whose diameter is the value obtained by adding the long diameter to the short diameter thereof, followed by dividing by 2, and the diameter of the imaginary circle is defined as "imaginary diameter of the bubble". Therefore, "the total area occupied by bubbles having an imaginary diameter of 5 mm or more" refers to the sum obtained by selecting all the bubbles having an imaginary diameter defined as described above of 5 mm or more and present on the surface of the side of the predetermined sheet which is in contact with the skin, and calculating the area of the imaginary circle based on the imaginary diameter. Then, the value of the total area is divided by the surface area of the predetermined sheet which is determined as 100% to determine the value of "the total area occupied by bubbles having an imaginary diameter of 5 mm or more in 100% of the surface area of the adhesive sheet for affixation to the body (%)".

Note that, in the adhesive sheet for affixation to the body of the present invention, such fine bubbles are present throughout the entire sheet. That is, the bubbles are present not only on the surface of the adhesive sheet for affixation to the body of the present invention, but also inside the sheet. Therefore, also in the cross-sectional surface of the adhesive sheet for affixation to the body, regarding the bubbles present on the cross-sectional surface, the value of the total area occupied by bubbles having an imaginary diameter of 5 mm or more in 100% of the cross-sectional surface (%) indicates the same value as the total area occupied by bubbles having an imaginary diameter of 5 mm or more in 100% of the surface area of the adhesive sheet for affixation to the body (%). That is, although the bubbles contained in the adhesive sheet for affixation to the body originally have a three-dimensional shape, the bubbles present on the surface of the sheet are visually confirmed as a planar shape. In the present invention, this is considered as the bubbles projected onto the surface of the adhesive sheet for affixation to the body and the value of "the total area occupied by bubbles having an imaginary diameter of 5 mm or more" is used to define the bubbles of specific conditions contained in the adhesive sheet for affixation to the body of the present invention.

In 100% of the surface area of the adhesive sheet for affixation to the body of the present invention, the total area occupied by bubbles having an imaginary diameter of 5 mm or more is 10% or less, preferably 5% or less, and more preferably, the adhesive sheet for affixation to the body of the present invention contains no bubble having an imaginary diameter of 5 mm or more in 100% of the surface area of the adhesive sheet for affixation to the body, from the viewpoint of the smoothness and adhesiveness of the sheet surface.

The adhesive sheet for affixation to the body of the present invention contains water as component (B). The content of the water of component (B) is preferably from 60 to 95% by mass, more preferably from 65 to 95% by mass, and still preferably from 70 to 90% by mass in 100% by mass in total of the adhesive sheet for affixation to the body of the present invention, from the viewpoint of incorporating a high concentration of carbon dioxide gas into the adhesive sheet for affixation to the body.

The adhesive sheet for affixation to the body of the present invention is preferably a sheet composed of an aqueous gel layer supported on a support layer in terms of easier application. The adhesive sheet for affixation to the body of the present invention can be produced by, for example, a method in which a sheet is formed by an aqueous gel layer containing component (B) and this sheet is placed in a low gas-permeable container, and then carbon dioxide gas is filled in the container. The adhesive sheet for affixation to the body of the present invention can also be produced by methods in which carbon dioxide gas is dissolved in an aqueous gel layer upon or after forming a sheet, the obtained sheet is placed in a low gas-permeable container, and then, the gas in the container is removed or the gas in the container is further exchanged with carbon dioxide gas.

Note that, when the adhesive sheet for affixation to the body of the present invention is the sheet composed of the aqueous gel layer supported on the support layer, the aqueous gel layer may be supported on the support layer, the aqueous gel layer is preferably arranged on the support layer, and the aqueous gel layer is more preferably laminated on the support layer. This adhesive sheet for affixation to the body may be composed of an aqueous gel layer on which not only a support layer, but also a release layer is supported, and in this case, the release layer may be supported on a surface opposite to the support layer, and the release layer is preferably laminated on the aqueous gel layer.

The above aqueous gel layer may be any layer that can stably retain water and consists of the aqueous gel layer containing component (B). The aqueous gel layer preferably contains a cross-link structure formed by an anionic polymer, a crosslinking agent, and water, from the viewpoint of moldability. In the cross-link structure of the anionic polymer, the anionic polymer is subjected to a crosslinking reaction to form a dense net structure which becomes the basic skeleton of the aqueous gel layer. Since the aqueous gel layer formed by chemical crosslinking of the anionic polymer retains a large amount of water in the net structure and is swelling, it has moderate elasticity, extensibility, and softness.

Examples of the above anionic polymer include polymers having a carboxyl group, a sulfate group, or a phosphate group. Specific examples thereof include poly(meth)acrylic acids, carboxyvinyl polymers, and salts thereof; anionic cellulose derivatives such as carboxymethylcellulose and carboxyethylcellulose and salts thereof; carrageenan, alginic acids, and salts thereof, and anionic starch derivatives. Among them, it is preferable to contain at least one selected from the group consisting of carboxymethylcellulose, carrageenan, and salts thereof, from the viewpoint of obtaining an aqueous gel layer satisfying a particularly high water-retention amount, sufficient gel strength, and the softness which allows to conform to the unevenness or the movement of the skin.

The content of the anionic polymer in the adhesive sheet for affixation to the body of the present invention is preferably from 0.5 to 25% by mass, and more preferably from 3 to 10% by mass in the aqueous gel layer, from the viewpoint of adjusting the viscosity of a gel in an uncrosslinked state or increasing the shape retainability of a crosslinked gel by physically entangling the net structure of the anionic polymer.

Examples of the above crosslinking agent include metal ion compounds, cationic polymers, and polyfunctional epoxy compounds, and it may be appropriately selected depending on the reactivity with the functional group of the anionic polymer to be used. Examples of the metal ion compounds include oxides, hydroxides, and salts containing aluminum, magnesium, calcium, and potassium, and for example, one or two or more selected from the group consisting of aluminum hydroxide, potassium alum, aluminum sulfate, aluminum oxide, aluminum glycinate, aluminum acetate, aluminum lactate, aluminum stearate, hydrous aluminum silicate, aluminum metasilicate, magnesium aluminometasilicate, magnesium chloride, magnesium stearate, calcium carbonate, calcium hydroxide, kaolin, synthetic hydrotalcite, and potassium hydrate can be used. When carboxymethylcellulose or a salt thereof is selected as the anionic polymer, an aluminum ion compound such as magnesium aluminometasilicate and aluminum hydroxide is preferably used as a crosslinking agent.

The content of the crosslinking agent is preferably from 0.01 to 10% by mass, more preferably from 0.05 to 5% by mass, and still preferably from 0.1 to 2% by mass in the aqueous gel layer.

Note that, when the adhesive sheet for affixation to the body of the present invention is composed of the above aqueous gel layer containing the cross-link structure formed by the above anionic polymer, crosslinking agent, and water, these anionic polymer and crosslinking agent are considered to be crosslinked in the aqueous gel layer. In the present invention, the content of the anionic polymer and the crosslinking agent in the aqueous gel layer is the content in the case of assuming that each of them is independently present.

The adhesive sheet for affixation to the body of the present invention may appropriately contain, in addition to the above components, other components usually used in a cosmetic product, a medicament, or the like, for example, components other than the above components such as oily components, powder components, water-soluble polymers, thickening agents, film-forming agents, ultraviolet absorbers, metal ion sequestering agents, alcohols, saccharides, amino acid derivatives, organic amines, resin emulsions, blood circulation promoters, skin nutrifying agents, vitamins, antioxidants, antioxidant aids, preservatives, pigments, and fragrances, depending on applications thereof. For example, fragrances may also be used as the blood circulation promoter.

More specifically, for example, it is preferable to contain a TRPM8 agonist, from the viewpoint of improving the persistence of the blood circulation promoting effect. Among thermosensitive TRP channels present in the body, the TRPM8 agonist is the agonist acting on TRPM8 which is a cold receptor. The TRPM8 agonist is not limited as long as it is a compound which activates the TRPM8 channel. Examples thereof include menthol such as L-menthol and DL-menthol, menthane diol, cineole, menthyl glyceryl ether, menthyl lactate, menthyl succinate, menthyl glutarate, menthyl pyrrolidone carboxylate, ethyl menthane carboxamide, menthanecarbonyl glycine ethyl ester, menthyl ethylamino oxalate, menthone glycerin acetal, butylcyclohexanone, isopulegol, trimethyl isopropyl butanamide, menthoxypropanediol, camphor, and icilin; and plants, essential oils, or the like such as mentha oil, peppermint oil, spearmint oil, and eucalyptus oil containing the TRPM8 agonist may be used. These may be used alone or in combination of two or more. Among them, one or two or more selected from the group consisting of menthol, menthyl lactate, trimethyl isopropyl butanamide, menthoxypropanediol, camphor, and icilin are preferable, and menthol is more preferable, from the viewpoint of comfort and efficacy upon application.

The content of the TRPM8 agonist is preferably 0.15% by mass or more, more preferably 0.2% by mass or more, and still preferably 0.3% by mass or more in the total amount of the adhesive sheet for affixation to the body of the present invention, from the viewpoint of further enhancing the effect of the carbon dioxide gas of component (A), enhancing the blood circulation promoting effect, increasing the persistence, and obtaining a comfort tingling sensation. Also, the content of the TRPM8 agonist is preferably 3% by mass or less, more preferably 2% by mass or less, and still preferably 1% by mass or less in the total amount of the adhesive sheet for affixation to the body of the present invention, from the viewpoint of suppressing skin irritation. The content of the TRPM8 agonist is preferably from 0.15% by mass to 3% by mass, more preferably from 0.2 to 2% by mass, and still preferably from 0.3 to 1% by mass in the total amount of the adhesive sheet for affixation to the body of the present invention.

In the present invention, it is preferable to contain an ester oil as the oily component, from the viewpoint of improving the blood circulation promoting effect and usability. The ester oil is preferably a fatty acid ester or a fatty acid glyceride, from the viewpoint of improving the compatibility with the carbon dioxide gas of component (A) or the TRPM8 agonist. Preferred examples of the fatty acid ester include isononyl isononanoate, isopropyl isostearate, isostearyl isostearate, cetyl isooctanoate, isopropyl myristate, isostearyl myristate, isopropyl palmitate, octyl palmitate, and isostearyl palmitate. Examples of the fatty acid glyceride include triglyceride, diglyceride, and monoglyceride, and triglyceride is preferable. The fatty acids constituting triglyceride, diglyceride, and monoglyceride are not limited and are, for example, saturated fatty acids and unsaturated fatty acids having from 2 to 24 carbon atoms, and preferably saturated fatty acids and unsaturated fatty acids having from 4 to 18 carbon atoms, such as caproic acid, caprylic acid, capric acid, lauric acid, myristic acid, myristoleic acid, palmitic acid, palmitoleic acid, stearic acid, oleic acid, linoleic acid, α-linolenic acid, and γ-linolenic acid. Among them, component (C) is preferably at least one selected from the group consisting of glyceryl tri(caprylate/caprate), isononyl isononanoate, isopropyl myristate, isopropyl isostearate, and isopropyl palmitate, and more preferably glyceryl tri(caprylate/caprate).

The content of the above ester oil is preferably 0.01% by mass or more, more preferably 0.05% by mass or more, still preferably 0.1% by mass or more, preferably 3% by mass or less, more preferably 1% by mass or less, and still preferably 0.5% by mass or less in the total amount of the adhesive sheet for affixation to the body of the present invention, from the viewpoint of further increasing the blood circulation promoting effect. The content of the ester oil is preferably from 0.01 to 3% by mass, more preferably from 0.05 to 1% by mass, and still preferably from 0.1 to 0.5% by mass in the total amount of the adhesive sheet for affixation to the body of the present invention.

Further, the mass ratio of the TRPM8 agonist to the above ester oil (TRPM8 agonist/ester oil) is preferably from 0.5 to 10, more preferably from 1 to 8, and still preferably from 2 to 6, from the viewpoint of improving the permeability to the skin.

Note that the adhesive sheet for affixation to the body of the present invention preferably contains no ethanol. However, a trace to small amount (0.001% by mass or more) of ethanol may be inevitably mixed into the sheet, and in such a case, smaller amounts of ethanol are preferable. There are concerns that the ethanol not only causes the skin irritation particularly to the people with ethanol intolerance, but also accelerates rapid drying of the skin and this may result in the occurrence of cracking and the like of the skin. Thus, it is preferable to limit the content of ethanol in terms of persistence of blood circulation promotion without increasing the skin irritation of the adhesive sheet for affixation to the body of the present invention.

Specifically, the content of ethanol is preferably 5% by mass or less, more preferably 3% by mass or less, still preferably 1% by mass or less, still more preferably 0.1% by mass or less, and still further preferably contains substantially no ethanol in the total amount of the adhesive sheet for affixation to the body of the present invention.

The thickness of the adhesive sheet for affixation to the body is preferably 0.5 mm or more, more preferably 0.7 mm or more, and still preferably 1 mm or more, from the viewpoint of blood circulation promoting effect, carbon dioxide gas retainability, and affixability. The thickness of the adhesive sheet for affixation to the body is preferably 3 mm or less, and more preferably 2 mm or less, from the viewpoint of affixability.

When the adhesive sheet for affixation to the body of the present invention contains the aqueous gel layer supported on the support layer, a sheet base material such as woven fabric, non-woven fabric, knitted fabric, synthetic resin film, and waterproof paper can be used as the support layer, and a laminate formed by laminating a plurality of them can also be used. Specifically, woven fabric or non-woven fabric of synthetic fibers such as nylon, polypropylene, polyester, polyethylene, polystyrene, polyurethane, and polyolefin, or of natural fibers consisting of silk, cotton, hemp, rayon, collagen, and the like; sheets of nylon, polypropylene, polyester, polyethylene, polyurethane, and the like; or thin-film sheet of pullulan, starch, and the like can be used. Among them, it is preferable to use woven fabric or non-woven fabric, and it is more preferable to use non-woven fabric, from the viewpoint of the contribution to suppress the size of the bubbles so as to satisfy the above bubble fraction and ensuring favorable affixability to the body.

The thickness of the support layer is from about 0.05 to 2.0 mm, and the surface of the support layer may be subjected to hydrophilic treatment or hydrophobic treatment.

It was revealed by the present inventor that, when a conventional sheet containing carbon dioxide gas as bubbles and composed of an aqueous gel layer supported on the support layer is affixed to the parts such as the arm and leg which occupy a wide area of the body, the sheet surface, specifically, the aqueous gel layer is likely to be peeled off from the affixation part. It is considered that this is because, the size of the bubbles is not controlled and non-uniform, and coarse bubbles are also intermixed in the conventional sheet, which causes unevenness on the surface of the aqueous gel layer and reduces the adhesion area between the aqueous gel layer and the affixation part. The present inventor has also revealed that it was required to further laminate a resin film and the like having low gas permeability and relatively high rigidity to suppress the outflow of carbon dioxide gas in such a conventional sheet, and thus, the softness of the sheet itself and the conformability to the movement of the body are poor and the use thereof by affixing to the body is limited to a narrow area or part such as the area around the eyes.

On the contrary, since the bubbles containing carbon dioxide gas are controlled such that the bubbles having a diameter of 5 mm or more may be 10% or less in the adhesive sheet for affixation to the body of the present invention, the smoothness of the surface of the sheet is increased even when the sheet constitutes the aqueous gel layer. Further, control of the particle diameter of the bubbles as described above allows to retain favorable softness and conformability to the affixation part when soft sheets such as (non-)woven fabrics are used as the support layer, which allows the sheet to be applied to a wide area of the body such as large parts or parts with intense movement.

Therefore, a tensile strength at 10% elongation of the support layer is preferably 20 N/50 mm or less, and more preferably 10 N/50 mm or less, from the viewpoint of improving conformability of the adhesive sheet for affixation to the body of the present invention to the body and enlarging the application area to the body. Specifically, among the above support layers, one selected from the group consisting of woven fabric and non-woven fabric is preferable. Note that the tensile strength can be measured according to the measurement method described in JIS L 1913: 2010.

Further, the above conventional sheet was obliged to use a sheet having low contractility such as plastics as the support layer to prevent the release of the carbonic acid gas from bubbles, and thus conformability and the like are poor and it was difficult to be used for the large portion of the body. However, since the adhesive sheet for affixation to the body of the present invention has fine bubbles and can contain a large amount of carbon dioxide gas in the sheet, it can impart a sufficient blood circulation promoting effect even when using a sheet having high contractility.

The adhesive sheet for affixation to the body of the present invention may be a sheet composed of an aqueous gel layer further supported on a release layer. The release layer (sheet or film) can be supported on or laminated on a surface of the aqueous gel layer opposite to the support layer which is supported on the aqueous gel layer to protect the affixing surface. The base material of the release layer (sheet or film) is not particularly limited, and examples thereof include polyester films such as polyethylene terephthalate film and polybutylene terephthalate film; polyolefin films such as polyethylene film and polypropylene film; and laminate papers obtained by laminating a plastic such as polyethylene on a paper such as kraft paper, glassine paper, and high-quality paper.

The adhesive sheet for affixation to the body of the present invention is sealed in low gas-permeable containers such as glass or plastic container, so-called packaging pillows, in addition to enclosed containers such as aluminum pillow. This allows to dissolve the above content of carbon dioxide gas in the adhesive sheet for affixation to the body and to maintain the state where carbon dioxide gas is dissolved.

The content of carbon dioxide gas in 100% by mass in total of the gas present in the low gas-permeable container is preferably 30% by mass or more, and more preferably 60% by mass or more, from the viewpoint of allowing the bubbles satisfying the above bubble fraction to be present while increasing the dissolved carbon dioxide gas concentration in the sheet. The content of carbon dioxide gas in 100% by mass in total of the gas present in the low gas-permeable container is preferably 93% by mass or less, and more preferably 90% by mass or less, from the viewpoint of controlling the size of the bubbles to satisfy the above bubble fraction and obtaining the persistent blood circulation promoting effect.

Note that the gas present in the low gas-permeable container refers to both the gas in the space portion of the container and the gas in the bubbles.

The content of carbon dioxide gas in 100% by mass in total of the gas present in the low gas-permeable container refers to the value calculated as follows. First, an adhesive sheet for affixation to the body packaged by filling carbon dioxide gas in a low gas-permeable container is aged for 24 hours. Thereafter, the oxygen concentration in the container reached equilibrium is measured to calculate the carbon dioxide gas concentration in the container from the obtained value. Specifically, the oxygen concentration in the container (F %) is measured by using a zirconia type oxygen concentration meter LS-450F (manufactured by TORAY ENGINEERING Co., Ltd). Since the oxygen concentration in the air is 20.6%, the percentage of the air in the container (G%) can be determined by the equation: (F/20.6)×100. Assuming that gas other than the air is carbon dioxide gas, the carbon dioxide gas concentration in the container (H %) is defined by the equation: 100−G.

In the adhesive sheet for affixation to the body housed in a container of the present invention, the volume percentage of the carbon dioxide gas present in the low gas-permeable container is calculated from the internal capacity of the low gas-permeable container defined below. Then, the volume percentage is preferably 5% or more, more preferably 10% or more, and still preferably 16% or more per 100% of the volume obtained by subtracting the volume of the sheet from the internal capacity of the low gas-permeable container, from the viewpoint of allowing the bubbles satisfying the above bubble fraction to be present while increasing the dissolved carbon dioxide gas concentration in the sheet. The content of carbon dioxide gas in 100% by mass in total of the gas present in the low gas-permeable container is preferably 30% or less, more preferably 25% by mass or less, and still preferably 19% or less per 100% of the internal capacity of the low gas-permeable container, from the viewpoint of controlling the size of the bubbles to satisfy the above bubble fraction and obtaining the persistent blood circulation promoting effect. As used herein, the internal capacity of the low gas-permeable container refers to a value of the volume calculated from the inner surface area of the low gas-permeable container and the value obtained by appropriately adding a correction depending on the shape of the container. Specifically, when the shape of the container is a cube, the surface area of the cube S [cm$^2$] is 6 times the square of X when one side is X cm, and thus, S is 6 X$^2$ and that is, X is the half power of (S/6). Then, the volume of the cube (the internal capacity of the low gas-permeable container) V [cm$^3$] is the cube of X, and thus, V is X$^3$. That is, when the shape is a cube, the internal capacity of the low gas-permeable container V is determined as the value of the 3/2 power of (S/6).

Thus, in the present invention, the internal capacity of the low gas-permeable container refers to the value of the volume calculated from the inner surface area of the low gas-permeable container. That is, considering the inner surface area of the low gas-permeable container as a cube having the same surface area, the value of the internal capacity of the low gas-permeable container is determined from the value of the volume occupied by this cube.

Note that the gas present in the low gas-permeable container refers to the gas in the space portion in the container excluding the bubbles present in the adhesive sheet for affixation to the body housed in a container. Also, carbon dioxide gas present in the low gas-permeable container refers to carbon dioxide gas present in the gas of the space portion in the container excluding carbon dioxide gas present in the adhesive sheet for affixation to the body housed in a container. As used herein, the total volume of the gas present in the low gas-permeable container can be measured by the Archimedes method, and the volume percentage of carbon dioxide gas present in the low gas-permeable container can be determined by using the method for determining the carbon dioxide gas concentration in the container mentioned above and excluding carbon dioxide gas present in the adhesive sheet for affixation to the body housed in a container. Specifically, it is only required to use the following equation.

Volume percentage of carbon dioxide gas present in low gas-permeable container (%)={((gas volume in container [cm$^3$]×(content of carbon dioxide gas in 100% by mass in total of gas in container [%]/100))÷(internal capacity of container−volume of adhesive sheet for affixation to body))}×100

The low gas-permeable container needs to have low carbon dioxide gas permeability. As used herein, low permeability refers to a carbon dioxide gas transmission rate of 50 cc/m$^2$·day·atm (ASTM D-1434) or less, and the low gas-permeable container preferably has impermeability. Further, the low gas-permeable container is more preferably a container consisting of materials having heat seal properties, and specific examples of the material include a laminate film obtained by laminating an aluminum foil, a laminate film having an aluminum vapor deposition layer, polyvinylidene chloride film, and a laminate film containing a polyvinylidene chloride layer. The form of the low gas-permeable container is preferably a flat bag, a gusset, and the like.

In the adhesive sheet for affixation to the body sealed in the low gas-permeable container, the volume percentage of the adhesive sheet for affixation to the body per 100% of the internal capacity of the low gas-permeable container (referred to as a filling ratio) is preferably 40% or less, more preferably 35% or less, and still preferably 25%, or less, from the viewpoint of allowing a high concentration of carbon dioxide to be dissolved in the sheet even in the storage and transport of the adhesive sheet for affixation to the body. The volume percentage of the adhesive sheet for affixation to the body per 100% of the internal capacity of the low gas-permeable container (filling ratio) is preferably 0.1% or more, more preferably 0.5% or more, and still preferably 1% or more, from the viewpoint of the effective utilization of space of the low gas-permeable container and cost reduction in storage, transport, and production. Further, when the form of the low gas-permeable container has a thin packaging form using four-side sealing, the above filling ratio is preferably from 1 to 20%, and when it has a packaging form having a thickness, the above filling ratio is preferably from 0.1 to 10%.

The adhesive sheet for affixation to the body of the present invention can provide the blood circulation promoting effect by opening the low gas-permeable container and taking out the sheet upon application, and when the adhesive sheet for affixation to the body is supported on the release layer, by peeling the release layer to affix the surface of the exposed sheet on the desired part of the body. Preferred examples of the application part of the adhesive sheet for affixation to the body of the present invention include the body other than the scalp, such as the foot, arm, shoulder, and waist, and the sheet is directly affixed on the part. The time for affixation and application is not particularly limited, and is preferably 15 minutes or more, and more preferably 30 minutes or more. For example, it can be affixed before bedtime and can continue to be applied through bedtime.

The adhesive sheet for affixation to the body of the present invention enables to clearly feel efficacies such as a tingling sensation or a warm sensation, and efficacy can be strongly felt even when it is used as a sheet for affixation to relatively less sensitive portions, specifically the leg such as the calf, the ankle, and the sole of the foot, resulting in a preferable sheet. It is also preferable as a sheet for blood circulation promotion because an excellent blood circulation promoting effect can be obtained. Further, since the adhesive sheet for affixation to the body of the present invention has high adhesiveness and is thereby excellent in affixability, it has high usability as a sheet for applying to large parts in the body such as the arm and leg or parts with intense movement.

When the adhesive sheet for affixation to the body of the present invention is a sheet composed of the aqueous gel layer supported on the support layer and the like, it can be obtained by a production method containing, for example, the following steps (I) to (III):

(I) a step of mixing gel layer-forming components and water (B) to prepare an aqueous gel containing bubbles;

(II) a step of spreading the obtained aqueous gel on a support by a coater through which a support layer is inserted to form an aqueous gel layer supported on the support layer and containing the bubbles; and (III) a step of accommodating, in a low gas-permeable container, a sheet composed of the aqueous gel layer supported on the support layer and containing the bubbles, and then injecting carbon dioxide gas into and sealing the container, allowing incorporation of bubbles containing carbon dioxide gas (A).

The above step (I) is a step of mixing gel layer-forming components and water (B) to prepare an aqueous gel containing bubbles. Examples of the gel layer-forming components include the anionic polymer and the crosslinking agent mentioned above. Specifically, in addition to using the anionic polymer, the crosslinking agent, and water as the components constituting the aqueous gel layer other than the carbon dioxide gas of component (A), an oil agent or the TRPM8 agonist is used if necessary, and these components are mixed by, for example, a mixer to prepare the aqueous gel containing bubbles. As used herein, regarding mixing conditions, it is preferable to be mixed at a pressure equal to or higher than the pressure of (atmospheric pressure −0.1 MPa), and more preferable to be mixed at atmospheric pressure without reducing the pressure, from the viewpoint of allowing incorporation of a lot of bubbles. In the present invention, bubbles of carbon dioxide gas in which the size of the bubbles is controlled to the above specific range are allowed to be present in the sheet to be obtained by performing step (I) under the above pressure conditions. The stirring time during mixing is preferably from 1 to 60 minutes, and more preferably from 5 to 30 minutes, from the viewpoint of efficient production. The stirring rate during mixing is preferably from 10 to 40 rpm (revolution/minute), and more preferably from 15 to 35 rpm from the viewpoint of allowing incorporation of a lot of bubbles. The mixer to be used is not particularly limited, and is preferably a planetary mixer which allows mixing by rotation and revolution, from the viewpoint of efficiently introducing a lot of bubbles.

The above step (II) is a step of spreading the aqueous gel obtained in step (I) by a coater through which the support layer is inserted to form the aqueous gel layer supported on the support layer and containing bubbles. When the aqueous gel is spread by a coater through which the support layer is inserted, the aqueous gel may be sandwiched between two sheets such as a non-woven fabric and a PET film and spread uniformly. The means thereof is not particularly limited, but it is preferable to use a roll coater as a coater, and more preferable to use a two-roll coater, from the viewpoint of forming a smooth aqueous gel layer. The two-roll coater can insert the support layer between rolls and spread the aqueous gel while loading a certain strong pressure, and can form the aqueous gel layer while supporting the aqueous gel on the support layer and maintaining the amount of bubbles. Examples of the two-roll coater include direct gravure coater, a chamber doctor coater, and a double roll coater.

It is preferable to retain the aqueous gel layer containing the bubbles obtained here for a certain time to promote ion crosslinking reaction in the aqueous gel for crosslinking. Upon retaining, the aqueous gel layer may be appropriately heated.

The above step (III) is a step of accommodating, in a low gas-permeable container, the sheet obtained in step (II) composed of the aqueous gel layer supported on the support layer and containing bubbles, and then injecting carbon dioxide gas into and sealing the container so that the content of carbon dioxide gas of the obtained sheet is from 100 to 20,000 ppm, allowing incorporation of bubbles containing carbon dioxide gas (A). As a method for injecting carbon dioxide gas, for example, the sheet composed of the aqueous gel layer supported on the support layer obtained in step (II) is placed in a low gas-permeable container such as a packaging pillow made of aluminum, and carbon dioxide gas is injected thereinto, followed by sealing. More specifically, carbon dioxide gas is injected into the container accommodating the sheet composed of the aqueous gel layer supported on the support layer obtained in step (II) so that the content of carbon dioxide gas in 100% by mass in total of the gas present in the container can be 30% by mass or more and 95% by mass or less.

Further, the sheet is preferably retained in the low gas-permeable container while being sealed until the start of using for several hours or more, and more specifically, it is preferably retained for 20 hours or more, and more preferably for 24 hours or more, from the viewpoint of completely dissolving carbon dioxide gas in the aqueous gel layer and allowing carbon dioxide gas to flow into the air present in the bubbles in the aqueous gel layer. Through such a step, carbon dioxide gas is dispersed into the aqueous gel layer and bubbles, resulting in the gel sheet which contains bubbles containing carbon dioxide gas. It is considered that carbon dioxide gas is dissolved into the aqueous gel layer in the sealed pillow by using the concentration gradient and further dispersed into bubbles, resulting in generation of bubbles containing carbon dioxide gas.

Note that the present invention can be described as the adhesive sheet for affixation to the body housed in a container, sealed in a low gas-permeable container which is produced through these steps and a part of the steps.

The adhesive sheet for affixation to the body of the present invention is preferably an adhesive sheet for affixation to the body housed in a container, containing the following components (A) and (B):

(A) bubbles containing carbon dioxide gas in a bubble fraction of 10% or more and 40% or less, and (B) water, wherein, the total area occupied by bubbles having an imaginary diameter of 5 mm or more is 10% or less, in 100% of the surface area of the adhesive sheet for affixation to the body, the content of carbon dioxide gas in the total amount of the adhesive sheet for affixation to the body is from 500 to 3,000 ppm, and the adhesive sheet for affixation to the body is sealed in a low gas-permeable container, from the viewpoint of effectively increasing affixability and conformability while retaining favorable smoothness as a sheet, exerting excellent effects on the fast-acting properties and persistence thereof while effectively enhancing the blood circulation promoting effect, and further imparting a preferred warm sensation upon application.

The adhesive sheet for affixation to the body of the present invention is also preferably an adhesive sheet for affixation to the body housed in a container, containing the following components (A) to (C):

(A) bubbles containing carbon dioxide gas in a bubble fraction of 10% or more and 40% or less;

(B) water, and (C) from 0.15 to 3% by mass of menthol, wherein the total area occupied by bubbles having an imaginary diameter of 5 mm or more is 10% or less, in 100% of the surface area of the adhesive sheet for affixation to the body, the content of carbon dioxide gas in the total amount of the adhesive sheet for affixation to the body is from 500 to 3,000 ppm, and the adhesive sheet for affixation to the body is sealed in a low gas-permeable container, from the viewpoint of effectively increasing affixability and conformability while retaining favorable smoothness as a sheet, exerting excellent effects on the fast-acting properties and persistence thereof while effectively enhancing the blood circulation promoting effect, and further imparting a preferred tingling sensation upon application.

Regarding the above-mentioned embodiments, the present invention further discloses the following adhesive sheet for affixation to the body housed in a container and a production method thereof.

[1] An adhesive sheet for affixation to the body housed in a container, containing the following components (A) and (B):

(A) bubbles containing carbon dioxide gas in a bubble fraction of 10% or more and 40% or less, and (B) water, wherein the total area occupied by bubbles having an imaginary diameter of 5 mm or more is 10% or less, in 100% of the surface area of the adhesive sheet for affixation to the body, a content of carbon dioxide gas in the total amount of the adhesive sheet for affixation to the body is from 100 to 20,000 ppm, and the adhesive sheet for affixation to the body is sealed in a low gas-permeable container.

[2] The adhesive sheet for affixation to the body housed in a container according to the above [1], containing the bubbles containing carbon dioxide gas of component (A) preferably in a bubble fraction of 15% or more, more preferably in a bubble fraction of 22% or more, still preferably in a bubble fraction of 25% or more, preferably in a bubble fraction of 38% or less, more preferably in a bubble fraction of 35% or less, and still preferably in a bubble fraction of 34% or less.

[3] The adhesive sheet for affixation to the body housed in a container according to the above [1] or [2], wherein the total area occupied by bubbles having an imaginary diameter of 5 mm or more is preferably 5% or less, and more preferably, the adhesive sheet for affixation to the body housed in a container contains no bubble having an imaginary diameter of 5 mm or more, in 100% of the surface area of the adhesive sheet for affixation to the body.

[4] The adhesive sheet for affixation to the body housed in a container according to any one of the above [1] to [3], wherein the content of carbon dioxide gas is preferably 200 ppm or more, more preferably 500 ppm or more, preferably 10,000 ppm or less, and more preferably 3,000 ppm or less.

[5] The adhesive sheet for affixation to the body housed in a container according to any one of the above [1] to [4], wherein the content of carbon dioxide gas in 100% by mass in total of the gas present in the low gas-permeable container is preferably 30% by mass or more, more preferably 60% by mass or more, preferably 93% by mass or less, and more preferably 90% by mass or less.

[6] The adhesive sheet for affixation to the body housed in a container according to any one of the above [1] to [5], wherein the content of the water of component (B) is preferably from 60 to 95% by mass, more preferably from 65 to 95% by mass, still preferably from 70 to 90% by mass in 100% by mass in total of the adhesive sheet for affixation to the body of the present invention.

[7] The adhesive sheet for affixation to the body housed in a container according to any one of the above [1] to [6], wherein the thickness is preferably 0.5 mm or more, more preferably 0.7 mm or more, still preferably 1 mm or more, preferably 3 mm or less, and more preferably 2 mm or less.

[8] The adhesive sheet for affixation to the body housed in a container according to any one of the above [1] to [7], wherein the adhesive sheet for affixation to the body housed in a container is a sheet composed of an aqueous gel layer supported on a support layer, or an aqueous gel layer supported on a support layer and a release layer.

[9] The adhesive sheet for affixation to the body housed in a container according to the above [8], wherein the aqueous gel layer preferably contains a cross-link structure formed by an anionic polymer, a crosslinking agent, and water.

[10] The adhesive sheet for affixation to the body housed in a container according to the above [8] or [9], wherein the anionic polymer is preferably a polymer having a carboxyl group, a sulfate group, or a phosphate group, and more preferably contains at least one selected from the group consisting of carboxymethylcellulose, carrageenan, and salts thereof.

[11] The adhesive sheet for affixation to the body housed in a container according to any one of the above [8] to [10], wherein a tensile strength at 10% elongation of the support layer is preferably 20 N/50 mm or less, and more preferably 10 N/50 mm or less.

[12] The adhesive sheet for affixation to the body housed in a container according to any one of the above [8] to [11], wherein the thickness of the support layer is from 0.05 to 2.0 mm.

[13] The adhesive sheet for affixation to the body housed in a container according to any one of the above [8] to [12], wherein the support layer is one or two or more selected from the group consisting of woven fabric, non-woven fabric, Angin, synthetic resin film, and waterproof paper, and is preferably one selected from the group consisting of woven fabric and non-woven fabric.

[14] A method for producing the adhesive sheet for affixation to the body housed in a container according to any one of the above [8] to [13], containing the following steps (I) to (III):

(I) a step of mixing gel layer-forming components and water (B) to prepare an aqueous gel containing bubbles;

(II) a step of spreading the obtained aqueous gel on a support by a coater through which a support layer is inserted to form an aqueous gel layer supported on the support layer and containing the bubbles; and (III) a step of accommodating, in a low gas-permeable container, a sheet composed of the aqueous gel layer supported on the support layer and containing the bubbles, and then injecting carbon dioxide gas into and sealing the container, allowing incorporation of bubbles containing carbon dioxide gas (A).

[15] The method for producing the adhesive sheet for affixation to the body housed in a container according to [14], wherein the coater used in step (II) is preferably a roll coater, and more preferably a two-roll coater.

EXAMPLES

Hereinafter, the present invention will be specifically described with reference to Examples. Note that the content of each component indicates % by mass, unless otherwise indicated in Table.

Example 1 to 7 and Comparative Example 1 to 4

According to the formulation shown in the following Table 1, each sheet for affixation was produced according to the following method.

Specifically, according to the formulation shown in the following Table 1, carboxymethylcellulose, polyvinyl alcohol, aluminum hydroxide, glycerin, and methyl parahydroxybenzoate were blended into the aqueous succinic acid solution at atmospheric pressure and the mixture was charged into a planetary mixer. Thereafter, for Examples 1 to 4 and Comparative Example 1, propylene glycol having the TRPM8 agonist and glyceryl tri(caprylate/caprate) (manufactured by Kao Corporation) dissolved therein by heating was added thereto and mixed to prepare an uncrosslinked gel. In all the formulation, the stirring speed during mixing was 33 rpm. A lot of bubbles were seen in the obtained uncrosslinked gel. The obtained uncrosslinked gel was sandwiched between a polyethylene film and a nonwoven fabric and spread by a two-roll coater so that the thickness of the aqueous gel could be 2 mm.

The obtained gel sheet was die-cut to a size of 12.5×8.5 cm (area: 106.25 cm$^2$, volume: 21.25 cm$^3$) and accommodated in an aluminum pillow having a size of 15×11 cm (volume: 407 cm$^3$). Each of them was filled by 60 mL or more of the gas containing a specific concentration of carbon dioxide gas to replace 90% or more of the atmosphere in the aluminum pillow with carbon dioxide gas, and then enclosed by heat sealing, followed by retaining 5 days to obtain a sheet for affixation.

Each measurement and evaluation were performed by using each of the obtained sheet for affixation according to the following methods and criteria.

Note that the volume percentage of carbon dioxide gas in 100% of the volume obtained by subtracting the volume of the sheet from the internal capacity of the container (%), the gas volume in a container (cm$^3$), the total area occupied by bubbles having an imaginary diameter of 5 mm or more in 100% by mass of the sheet for affixation (%), the bubble fraction (%), and the content of carbon dioxide gas in 100% by mass in total of the gas in the container (% by mass) were measured by the above-mentioned methods at room temperature of 25° C. and relative humidity of 50%. When all the bubbles present on the surface of the side of the sheet for affixation which is to be in contact with the skin were selected, specifically, the surface of the sheet for affixation which is affixed to the skin was observed from above and all the bubbles whose presence can be visually confirmed were selected.

Table 1 shows the results of each measurement and evaluation.

<Measurement of Carbon Dioxide Gas Concentration in Sheet for Affixation>

The carbon dioxide gas concentration in the sheet for affixation was measured immediately after opening the aluminum pillow and at a point of time when 5 minutes have passed immediately after opening.

Specifically, the sheet for affixation was immersed in a bottle with lid containing an alkaline solution to dissolve the gel. Then, it was acidified again by an acidic buffer solution (pH 4.5) and a carbon dioxide gas electrode (CE-2041; manufactured by DKK-TOA CORPORATION) was used to measure the generated carbon dioxide gas. The carbon dioxide gas concentration in the sheet for affixation was calculated from the obtained carbon dioxide gas concentration. The value of the carbon dioxide gas concentration can be used as an index of the evaluation of the retainability of carbon dioxide gas in the obtained sheet.

<Blood Flow Increase Rate>

After acclimatizing the forearm of a professional panelist in advance at 25±1° C. and humidity of 50±5% for 20 minutes, the blood flow of the inner side of the forearm was measured by using a laser speckle blood flow meter and this was used as the value before application of the sheet for affixation.

After the aluminum pillow was opened and each sheet for affixation was immediately affixed on the inner side of the forearm of a professional panelist, the blood flow was measured 5 minutes, 10 minutes, and 30 minutes after affixation to determine the increasing rate (%) where the blood flow rate before application was taken as 100. The value of the increasing rate (%) can be used as an index of the evaluation of the blood circulation promoting action and the persistence of the obtained sheet.

<Evaluation of Tingling Sensation and Warm Sensation>

The aluminum pillow was opened and each sheet for affixation was immediately affixed on each calf of one professional panelist. Then, the tingling sensation and the warm sensation 5 minutes, 10 minutes, and 30 minutes after affixation were evaluated according to the following criteria. The values can be used as an index of the evaluation of the sensation which reminds a comfort sensation of stimulation and blood circulation promotion upon application of the obtained sheet, and a higher numerical value represents a more excellent performance.

7: Felt very strongly.
6: Felt strongly.
5: Felt somewhat strongly.
4: Felt clearly.
3: Felt.
2: Felt slightly.
1: Felt nothing.

<Evaluation of Adhesiveness>

The aluminum pillow was opened and each sheet for affixation was immediately affixed on the calf of a professional panelist and the panelist performed plantarflexion and dorsiflexion of the ankle ten times. Then, the percentage of the area of the sheet for affixation which was suspended (peeled) from the affixed calf in the total area of the sheet for affixation (%) was determined and evaluated according to the following criteria, and this was used as an index of the evaluation of the adhesiveness (affixability and conformability). A higher numerical value of the evaluation represents a more excellent effect.

6: More than 0% and 10% or less
5: More than 10% and 20% or less
4: More than 20% and 30% or less
3: More than 30% and 40% or less
2: More than 40% and 50% or less
1: More than 50%

TABLE 1

| Layer configuration | Component | Example 1 | Example 2 | Example 3 | Example 4 | Comparative Example 1 | Example 5 | Example 6 | Example 7 | Comparative Example 2 | Comparative Example 3 | Comparative Example 4 |
|---|---|---|---|---|---|---|---|---|---|---|---|---|
| Aqueous gel layer | Carboxymethylcellulose | 3.5 | 3.5 | 3.5 | 3.5 | 3.5 | 3.5 | 3.5 | 3.5 | 3.5 | 3.5 | 3.5 |
| | Polyvinyl alcohol | 5 | 5 | 5 | 5 | 5 | 5 | 5 | 5 | 5 | 5 | 5 |
| | Aluminum hydroxide | 0.05 | 0.05 | 0.05 | 0.05 | 0.05 | 0.05 | 0.05 | 0.05 | 0.05 | 0.05 | 0.05 |
| | Magnesium aluminometasilicate | 0.05 | 0.05 | 0.05 | 0.05 | 0.05 | 0.05 | 0.05 | 0.05 | 0.05 | 0.05 | 0.05 |
| | Succinic acid | 0.4 | 0.4 | 0.4 | 0.4 | 0.4 | 0.4 | 0.4 | 0.4 | 0.4 | 0.4 | 0.4 |
| | Methyl parahydroxybenzoate | 0.25 | 0.25 | 0.25 | 0.25 | 0.25 | 0.25 | 0.25 | 0.25 | 0.25 | 0.25 | 0.25 |
| | Glycerin | 10 | 10 | 10 | 10 | 10 | 10 | 10 | 10 | 10 | 10 | 10 |
| | Propylene glycol | 5 | 5 | 5 | 5 | 5 | 5 | 5 | 5 | 5 | 5 | 5 |
| | Menthol | 0.4 | — | — | 0.4 | 0.4 | — | — | — | — | — | — |
| | Glyceryl tri(caprylate/caprate) | 0.1 | — | — | 0.1 | 0.1 | — | — | — | — | — | — |
| | Purified water | 75.25 | 75.25 | 75.25 | 75.25 | 75.25 | 75.75 | 75.75 | 75.75 | 75.75 | 75.75 | 75.75 |
| | Total | 100 | 100 | 100 | 100 | 100 | 100 | 100 | 100 | 100 | 100 | 100 |
| | Support layer | Non-woven fabric | Non-woven fabric | Non-woven fabric | Non-woven fabric | Non-woven fabric | Non-woven fabric | Non-woven fabric | None | Non-woven fabric | Non-woven fabric | Resin film |
| Evaluation | Gas volume in container [cm³] | 17 | 16 | 12 | 16 | 18 | 17 | 18 | 15 | 20 | 17 | 18 |
| Volume percentage of carbon dioxide gas with respect to volume obtained by subtracting volume of sheet from internal capacity of container (%) | | 78 | 75 | 65 | 69 | 75 | 79 | 76 | 69 | 81 | 75 | 72 |
| Total area occupied by bubbles having an imaginary diameter of 5 mm or more in 100% of surface area of sheet (%) | | 0.0 | 0.3 | 1.1 | 4.0 | 15.0 | 0.0 | 73 | 3.2 | 12.0 | 0.0 | 21.0 |
| Bubble fraction of (A) bubbles containing carbon dioxide gas (%) | | 32 | 20 | 14 | 35 | 36 | 28 | 36 | 30 | 39 | 4 | 30 |
| Content of carbon dioxide gas in 100% by mass in total of gas in container (% by mass) | | 85 | 80 | 72 | 88 | 95 | 85 | 89 | 86 | 97 | 86 | 95 |
| (B) moisture amount | | 75.25 | 75.25 | 75.25 | 75.25 | 75.25 | 75.75 | 75.75 | 75.75 | 75.75 | 75.75 | 75.75 |
| Carbon dioxide gas concentration in the sheet (ppm) | Initial | 1576 | 1559 | 1443 | 1775 | 1860 | 1550 | 1749 | 1621 | 1779 | 1065 | 2090 |
| | After 5 minutes | 803 | 768 | 730 | 840 | 410 | 786 | 698 | 711 | 345 | 325 | 879 |
| | Carbon dioxide gas concentration retention rate (%) | 51 | 49 | 51 | 47 | 22 | 51 | 40 | 44 | 19 | 31 | 42 |
| Blood circulation enhancing effect | Blood flow increase rate (%) After 5 minutes | 216 | 185 | 161 | 184 | 162 | 164 | 160 | 171 | 145 | 131 | 184 |
| | After 10 minutes | 183 | 150 | 138 | 177 | 119 | 137 | 149 | 145 | 115 | 119 | 143 |
| | After 20 minutes | 140 | 129 | 121 | 131 | 104 | 104 | 109 | 115 | 98 | 104 | 106 |
| | Tingling sensation After 5 minutes | 3.0 | 3.0 | 3.0 | 3.0 | 2.0 | 3.0 | 3.0 | 3.0 | 2.0 | 2.0 | 3.0 |
| | After 10 minutes | 4.0 | 4.0 | 3.0 | 3.0 | 3.0 | 2.0 | 2.0 | 2.0 | 1.0 | 1.0 | 2.0 |
| | After 20 minutes | 5.0 | 5.0 | 5.0 | 5.0 | 4.0 | 1.0 | 1.0 | 1.0 | 1.0 | 1.0 | 1.0 |
| | Warm sensation After 5 minutes | 3.0 | 3.0 | 3.0 | 3.0 | 3.0 | 3.0 | 3.0 | 3.0 | 2.0 | 2.0 | 3.0 |
| | After 10 minutes | 1.0 | 1.0 | 1.0 | 1.0 | 1.0 | 2.0 | 2.0 | 2.0 | 1.0 | 1.0 | 1.0 |
| | After 20 minutes | 1.0 | 1.0 | 1.0 | 1.0 | 1.0 | 2.0 | 2.0 | 2.0 | 1.0 | 1.0 | 2.0 |
| | Adhesiveness | 7.0 | 6.0 | 6.0 | 6.0 | 2.0 | 7.0 | 5.0 | 7.0 | 2.0 | 6.0 | 2.0 |

Table 1 shows the results that, for example, in Examples 5 to 7 containing bubbles containing carbon dioxide gas in a bubble fraction of from 10% to 40%, the blood flow increase rate maintained high values of 130% or more even in 10 minutes after use, whereas in Comparative Example 3 containing bubbles containing carbon dioxide gas in a bubble fraction of less than 10%, the blood flow increase rate in 10 minutes after use showed low values. It was also found that in Comparative Example 2 in which the total area occupied by bubbles having an imaginary diameter of 5 mm or more in 100% of the sheet surface area exceeds 10%, the blood flow increase rate after 10 minutes is low, and in Comparative Example 4, adhesiveness is poor and sufficient affixability and conformability cannot be obtained.

Among Examples, it was also found that, in Examples 1 to 4 containing menthol and glyceryl tri(caprylate/caprate) as an oil agent, a more excellent blood flow increase rate and a favorable tingling sensation can be obtained in addition to the retainability of the carbon dioxide gas concentration in the sheet and adhesiveness.

Regarding the evaluation of warm sensation, the results obtained showed that a more excellent warm sensation for a long period of time can be obtained in Examples 5 to 7 containing neither menthol nor an oil agent.

The invention claimed is:

1. An adhesive sheet composed of an aqueous gel layer supported on a support layer which consists of non-woven fabric, the adhesive sheet comprising the following components (A) and (B):
   (A) bubbles containing carbon dioxide gas in a bubble fraction of 10% or more and 40% or less when measured within 5 minutes after opening the container and taking out the sheet from the container, and
   (B) water,
   wherein a total area occupied by bubbles having an imaginary diameter of 5 mm or more when measured within 5 minutes after opening the container and taking out the sheet from the container is 10% or less, relative to 100% of a surface area of the adhesive sheet, a content of carbon dioxide gas present in a total amount of the adhesive sheet is from 100 to 20,000 ppm, and the adhesive sheet is sealed in a low gas-permeable container.

2. The adhesive sheet according to claim 1, comprising the bubbles containing carbon dioxide gas of component (A) in a bubble fraction of 15% or more and 38% or less.

3. The adhesive sheet according to claim 1, wherein the total area occupied by bubbles having an imaginary diameter of 5 mm or more is 5% or less, relative to 100% of the surface area of the adhesive sheet.

4. The adhesive sheet according to claim 1, wherein a content of the water of component (B) is from 60 to 95% by mass based on a total mass of the adhesive sheet.

5. The adhesive sheet according to claim 1, wherein the a aqueous gel layer is further supported on a release layer.

6. The adhesive sheet according to claim 5, wherein the aqueous gel layer comprises a cross-link structure formed by an anionic polymer, a crosslinking agent, and water.

7. The adhesive sheet according to claim 6, wherein the anionic polymer is a polymer having a carboxyl group, a sulfate group, or a phosphate group.

8. The adhesive sheet according to claim 5, wherein a tensile strength at 10% elongation of the support layer is 20 N/50 mm or less.

9. The adhesive sheet according to claim 5, wherein a thickness of the support layer is from 0.05 to 2.0 mm.

10. The adhesive sheet according to claim 1, wherein a content of carbon dioxide gas is from 30 to 90% by mass based on a total mass of gas present in the low gas-permeable container.

11. The adhesive sheet according to claim 1, wherein a content of carbon dioxide gas is from 60 to 90% by mass based on a total mass of gas present in the low gas-permeable container.

12. The adhesive sheet according to claim 1, wherein the, content of carbon dioxide gas present in the total amount of the adhesive sheet is from 200 to 10,000 ppm.

13. The adhesive sheet according to claim 1, which has a thickness of from 0.5 to 3 mm.

14. A method for producing the adhesive sheet according to claim 5, the method comprising:
   (I) mixing gel layer-forming components and water (B) to prepare an aqueous gel containing bubbles;
   (II) spreading the obtained aqueous gel on a support by a coater through which a support layer is inserted to form an aqueous gel layer supported on the support layer and containing the bubbles; and
   (III) accommodating, in a low gas-permeable container, a sheet comprising the aqueous gel layer supported on the support layer and containing the bubbles, and then injecting carbon dioxide gas into and sealing the container, thereby incorporating bubbles containing carbon dioxide gas (A).

15. The method according to claim 14, wherein the coater is a roll coater.

* * * * *